US012629368B2

(12) United States Patent
Callizot et al.

(10) Patent No.: US 12,629,368 B2
(45) Date of Patent: May 19, 2026

(54) USE OF N-(3-(4-(3-(DIISOBUTYLAMINO) PROPYL) PIPERAZIN-1-YL)PROPYL)-1H-BENZO[D]IMIDAZOL-2-AMINE SULPHATE SALTS AND SOLVATES THEREOF FOR THE TREATMENT OF MOTOR NEURON DISEASES AND NEUROMUSCULAR JUNCTION DISORDERS

(71) Applicant: ALZPROTECT, Loos (FR)

(72) Inventors: Noëlle Callizot, Aix-en-Provence (FR); Cécilia Estrella, Lille (FR); Mathieu Barrier, Ligny le Ribault (FR); Philippe Verwaerde, Santes (FR)

(73) Assignee: ALZPROTECT, Loos (FR)

( * ) Notice: Subject to any disclaimer, the term of this patent is extended or adjusted under 35 U.S.C. 154(b) by 474 days.

(21) Appl. No.: 18/044,697

(22) PCT Filed: Oct. 7, 2021

(86) PCT No.: PCT/EP2021/077641
§ 371 (c)(1),
(2) Date: Mar. 9, 2023

(87) PCT Pub. No.: WO2022/074093
PCT Pub. Date: Apr. 14, 2022

(65) Prior Publication Data

US 2023/0364076 A1 Nov. 16, 2023

(30) Foreign Application Priority Data

Oct. 7, 2020 (EP) .................................... 20306168

(51) Int. Cl.
*A61K 31/497* (2006.01)
*A61P 21/04* (2006.01)

(52) U.S. Cl.
CPC ............ *A61K 31/497* (2013.01); *A61P 21/04* (2018.01)

(58) Field of Classification Search
CPC .............................. A61K 31/497; A61P 21/04
See application file for complete search history.

(56) References Cited

U.S. PATENT DOCUMENTS

2008/0027039 A1 1/2008 Arakawa et al.

FOREIGN PATENT DOCUMENTS

| | | | |
|---|---|---|---|
| WO | 2006051489 | | 5/2006 |
| WO | 2014/111525 | | 1/2014 |
| WO | WO 2014/102339 | * | 7/2014 |
| WO | 2015/195822 | | 12/2015 |
| WO | 2022/069654 | | 4/2022 |
| WO | 2022/074093 | | 4/2022 |

OTHER PUBLICATIONS

International Search Report mailed Dec. 23, 2021 for International Application No. PCT/EP2021/077641, 4 pages.

McKee, Dr. Ann C. et al. "Chronic Traumatic Encephalopathy in Athletes: Progressive Tauopathy following Repetitive Head Injury" J. of Neuropathology and Experimental Neurology (2009) vol. 68(7), pp. 709-735.

Miller, Nimrod et al. "Non-Aggregating Tau Phosphorylation by Cyclin-Dependent Kinase 5 Contributes to Motor Neuron Degeneration in Spinal Muscular Atrophy" The Journal Neuroscience (2015) vol. 35(15)m pp. 6038-6050.

Dupuis, Luc et al. "Skeletal muscle in motor neuron diseases : therapeutic target and delivery route for potential treatments" Curr Drug Targets (2010) vol. 11(10), pp. 1250-1261.

Gromova, Anastasia et al. "Harmony Lost: Cell-Cell Communication at the Neuromuscular Junction in Motor Neuron Disease" Trends Neuroscience (2020) vol. 43(9), pp. 709-724.

Hashizume, Atsushi et al. "Disease mechanism, biomarker and therapeutics for spinal and bulbar muscular atrophy (SBMA)", J Neurol Neurosurg Psychiatry (2020) vol. 91(10), pp. 1085-1091.

Gilhus, Nils E. "Myasthenia and the neuromuscular junction" Curr Opin Neurol. (2012) vol. 25(5), pp. 523-529.

Hosokawa, Masato et al. Progranulin Reduction Is Associated With Increased Tau Phosphorylation in P301L Tau Transgenic Mice J. Neuropathol. Exp. Neurol. (2015) vol. 74(2), pp. 158-165.

Van Eijk, Ruben P.A. et al. "Current trends in the clinical trial landscape for amyotrophic lateral sclerosis" Current opinion in neurology (2020) vol. 33(5), pp. 655-661.

International Search Report (ISR) and Written Opinion for PCT/EP2021/077641 dated Dec. 7, 2021, pp. 1-9.

Yang, Yang "Progress in clinical treatment of motor neurone disease" Medical Equipment (2019) vol. 32(04), pp. 203-204.

Yoon-Cheol, Jeong et al. "Frontotemporal Dementia with Motor Neuron Disease in a Patient with Antiphospholipid Syndrome: A Case Report" Dement Neurocogn Disord. (2016) vol. 15(4), pp. 165-169.

Ryckebusch, Adina et al. "Synthesis and Antimalarial Evaluation of New 1,4-bis(3-aminopropyl)piperazine Derivatives" Bioorganic & Medicinal Chemistry Letters (2003) vol. 13(21), pp. 3783-3787.

International Search Report (ISR) for PCT/EP2022/086773 dated Apr. 4, 2023, pp. 1-5.

Wang, Zilai et al. "Presynaptic and postsynaptic interaction of the amyloid precursor protein promotes peripheral and central synaptogenesis" J Neurosci. (2009) vol. 29(35), pp. 10788-10801.

Feldman, Eva L. et al. "Atlas of Neuromuscular Diseases, A Practical Guideline, Second Edition" Motor Neuron Diseases (2014), pp. 290-293.

* cited by examiner

*Primary Examiner* — Marcos L Sznaidman
(74) *Attorney, Agent, or Firm* — McDonnell Boehnen Hulbert & Berghoff LLP

(57) ABSTRACT

The present invention relates to sulphate salts of N-(3-(4-(3-(diisobutylamino)propyl)piperazin-1-yl)propyl)-1H-benzo[d]imidazol-2-amine and pharmaceutically acceptable solvates thereof, for use in the treatment and/or prevention of motor neuron diseases and neuromuscular junction disorders.

14 Claims, 4 Drawing Sheets

Specification includes a Sequence Listing.

USE OF N-(3-(4-(3-(DIISOBUTYLAMINO)PROPYL) PIPERAZIN-1-YL)PROPYL)-1H-BENZO[D]IMIDAZOL-2-AMINE SULPHATE SALTS AND SOLVATES THEREOF FOR THE TREATMENT OF MOTOR NEURON DISEASES AND NEUROMUSCULAR JUNCTION DISORDERS

CROSS-REFERENCE TO RELATED APPLICATIONS

This application is a U.S. national phase of International Application No. PCT/EP2021/077641, filed Oct. 7, 2021, which claims priority from European Patent Application no. EP 20306168.4, filed Oct. 7, 2020, the disclosure of each of which is incorporated herein by reference in its entirety.

The present invention relates to novel uses of N-(3-(4-(3-(diisobutylamino)propyl)piperazin-1-yl)propyl)-1H-benzo[d]imidazol-2-amine sulphate salts and pharmaceutically acceptable solvates thereof, in the treatment and/or prevention of motor neuron diseases and neuromuscular junction disorders.

BACKGROUND OF THE INVENTION

Motor neuron diseases (MND) and neuromuscular junction disorders (NJD) are both considered neuromuscular disorders which lead to muscle weakness and weariness that becomes more pronounced over time.

Motor neurons are neuronal cells present in the central nervous system (motor cortex, brainstem, spinal cord . . . ) and in the peripheral nervous system responsible for controlling organs like muscles and glands. Motor neurons are classified as upper or lower motor neurons. Upper motor neurons (UMN) are located in the cerebral cortex and in the brainstem, they transmit signals to interneurons and to lower motor neurons (LMN) via glutamatergic neurotransmission. The LMN are located in the spinal cord and innervate skeletal muscle fibers (neuromuscular junctions) where acetylcholine is released to carry the signal across the muscle cell membrane, signaling the muscle to contract or relax. Both UMN and LMN are essential to voluntary movements, balance, body posture adjustment and muscle control in general.

Progressive motor neuron degeneration is the hallmark of motor neuron diseases, it eventually causes motor neuron apoptosis and fasciculation of the motor units (unit defining the motor neuron—its axon—the neuromuscular junction—the individual muscle fibers it innervates altogether), preventing transmission of nerve influx controlling muscles. Death of the cell bodies of motoneurons is the primary process in MND and it occurs in conjunction with deposition of aggregated proteins in motoneurons and oligodendrocytes, as well as neuroinflammation. These diseases which can either affect UMN or LMN and even both, cause muscle weakness, hypotonia, movement lowness, impairment of reflexes and muscle atrophy.

There are numerous motor neuron diseases and amyotrophic lateral sclerosis (ALS) is the most common acquired motor neuron disease that could affect UMN and LMN. Sporadic ALS is the most common form of ALS (≥90% of cases) diagnosed in patients with no known family members affected by the disease. Familial ALS are of genetic origin and run in families, several gene mutations have been identified and linked thereto. The most common is in the chromosome 9 open reading frame 72 (C9ORF72) and can cause patients to suffer from cognitive defects as well: ALS-FTD is a particular form of ALS where patients also suffer from frontotemporal dementia (FTD). Amyotrophic lateral sclerosis with parkinsonism-dementia complex 1 (ALS-PDC) or Lytico-bodig disease, is a form of ALS where patients experience symptoms of ALS, dementia, and Parkinson's disease (PD). Other known genes associated with familial and sporadic ALS include those encoding superoxide dismutase 1 (SOD1), TAR DNA binding protein of 43-kDa (TDP-43), RNA-binding protein (FUS/TLS: Fused in Sarcoma/Translocated in Sarcoma) and ubiquilin 2 (UBQLN2). These mutations can cause toxic accumulation of these proteins in the motor neurons and astrocytes, thus subsequently leading to neurons death. TAR DNA binding protein of 43-kDa (TDP-43) is shown to accumulate in the cytoplasm of motor neurons in most cases of ALS. TDP-43 is a nuclear RNA-binding protein involved in several aspects of RNA processing that actively shuttles between the nucleus and the cytoplasm. In ALS, TDP-43 is excluded from the nucleus, but such cytoplasmic mislocalization is common in neuronal injury or stress, and TDP-43-positive inclusions may represent a secondary pathology in motor neuron diseases.

Other motor neuron diseases can either affect the UMN only such as primary lateral sclerosis (PLS) or the LMN only such as progressive muscular atrophy (PMA). Moreover, LMN degeneration and ALS can affect the neuromuscular junction (Dupuis L et al *Curr Drug Targets* 2010; 11(10): 1250-1261—Gromova A et al, Trends Neurosci. 2020 September; 43(9):709-724—Hashizume A et al, J Neurol Neurosurg Psychiatry 2020 October; 91(10):1085-1091). NJD target this critical region and block the nerve impulse normally transmitted to a muscle to facilitate movement or its contraction. Myasthenic syndromes (myasthenia gravis and Eaton-Lambert syndrome) affect the efficacy of synaptic transmission through either immunological or genetic processes. In these pathologies, the absolute number of NMJs remain roughly the same but their efficacy to trigger a muscle action potential in response to motor neuron stimulation is decreased leading to fatigable muscle weakness (Gilhus N E et al Curr Opin Neurol. 2012 October; 25(5): 523-9). In addition, it is recognized that designing treatments to strengthen and stabilize the remaining NMJs, the common final pathway of diseases with LMN degeneration, would be equally beneficial for ALS, spinal muscular atrophy (SMA) and spinal-bulbar muscular atrophy (SBMA) patients.

Only one treatment is currently approved by the United States Food and Drug Administration (FDA) and the European Medicines Agency (EMA) for ALS patients. Riluzole is an oral drug that blocks glutamatergic neurotransmission in the CNS. It is thought these effects may be partly due to inactivation of voltage-dependent sodium channels on glutamatergic nerve terminals. Riluzole also blocks some of the postsynaptic effects of glutamic acid by noncompetitive blockade of N-methyl-D-aspartate (NMDA) receptors. Still, Riluzole has no effect on motor and respiratory functions and is neither suited for advanced forms of ALS nor for other motor neuron diseases.

The free radical scavenger Edavarone injected intravenously showed efficacy in a small subset of people with ALS in a phase 3 clinical trial. The study showed a significantly smaller decline of ALS Functional Rating Scale-Revised score compared with placebo. Up to now there is no indication that Edaravone might be effective in a wider population of patients with ALS who do not meet the criteria (Abe et al., *Lancet Neurol.* 2017, 16(7), 505-512) and the application for a marketing authorization from the EMA for ALS treatment was withdrawn.

No specific treatment is available for neuromuscular junction disorders besides corticosteroids or immunosuppressants which could have serious side effects.

N-(3-(4-(3-(diisobutylamino)propyl)piperazin-1-yl)propyl)-1H-benzo[d]imidazol-2-amine sulphate salts and solvates thereof, previously disclosed in WO 2014/102339 are useful for the treatment and/or prevention of neurodegenerative diseases, amyloidopathies, tauopathies and developmental disease. These compounds are especially of interest for Alzheimer's disease, Parkinson's disease and tauopathies: a phase 2A clinical trial with N-(3-(4-(3-(diisobutylamino)propyl)piperazin-1-yl)propyl)-1H-benzo[d]imidazol-2-amine di-sulphate salt for patients suffering from progressive supranuclear palsy (PSP) is ongoing. These salts are able to modulate Tau phosphorylation and increase progranulin (PGRN) neurotrophic factor levels which deficiency is known to accelerates Tau deposition and phosphorylation, as evidenced in human tau-expressing mice (*J. Neuropathol. Exp. Neurol.* 74, 158-165 (2015)). Therefore, these compounds are especially useful for the treatment of tauopathies such as fronto-temporal dementia and were thus proposed for treating ALS-FTD specifically.

Limited treatments are available to patients suffering from motor neuron diseases or neuromuscular junction disorders and there is still a need in the art for new chemical entities that could be used in the treatment or prophylaxis of these diseases, hence the Applicant investigated the potential of using N-(3-(4-(3-(diisobutylamino)propyl)piperazin-1-yl)propyl)-1H-benzo[d]imidazol-2-amine sulphate salts and solvates thereof for such purpose.

SUMMARY OF THE INVENTION

The present invention is based on the unexpected findings that sulphate salts of N-(3-(4-(3-(diisobutylamino)propyl)piperazin-1-yl)propyl)-1H-benzo[d]imidazol-2-amine have neuroprotective effects on motor neurons and neuromuscular junctions.

The invention thus concerns N-(3-(4-(3-(diisobutylamino)propyl)piperazin-1-yl)propyl)-1H-benzo[d]imidazol-2-amine sulphate salts and solvates thereof for use in the treatment and/or prevention of motor neuron diseases and neuromuscular junction disorders.

Moreover, the Applicant has shown that N-(3-(4-(3-(diisobutylamino)propyl)piperazin-1-yl)propyl)-1H-benzo[d]imidazol-2-amine sulphate salts and solvates thereof were able to reduce the abnormal translocation of TDP43 from the nucleus to the cytoplasm in motor neurons, a pathological feature observed in most ALS cases.

DETAILED DESCRIPTION OF THE INVENTION

Applicant has shown that N-(3-(4-(3-(diisobutylamino)propyl)piperazin-1-yl)propyl)-1H-benzo[d]imidazol-2-amine sulphate salts and pharmaceutically acceptable solvates thereof exert beneficial effects on primary culture of both wild-type rat and SOD1$^{G93A}$ tg rat spinal cord motor neurons, by promoting their survival and the integrity of their neurite network after glutamate-induced damages. Furthermore, abnormal translocation of TDP-43 from the nucleus to the cytoplasm of motor neurons is a pathological feature observed in most ALS cases. The results presented in the examples section show that said sulphate salts could also reverse the abnormal translocation of TDP-43 from the nucleus to the cytoplasm under glutamatergic stress.

Moreover, N-(3-(4-(3-(diisobutylamino)propyl)piperazin-1-yl)propyl)-1H-benzo[d]imidazol-2-amine sulphate salts and pharmaceutically acceptable solvates thereof successfully protected the neuromuscular junctions and the neurite network against the glutamatergic stress in a co-culture of myoblasts and spinal cord explants.

All these findings support that N-(3-(4-(3-(diisobutylamino)propyl)piperazin-1-yl)propyl)-1H-benzo[d]imidazol-2-amine sulphate salts and pharmaceutically acceptable solvates thereof could be an effective therapy to improve motor neuron diseases such as ALS, SMA and SBMA as well as neuromuscular junction disorders like myasthenia gravis and Eaton-Lambert syndrome.

Motor neuron diseases and neuromuscular junction disorders include, but are not limited to non-FTD amyotrophic lateral sclerosis, primary lateral sclerosis (PLS), hereditary spastic paraplegia (HSP), neurolathyrism, Konzo, Tay-Sachs disease, Sandhoff disease, progressive muscular atrophy (PMA), monomelic amyotrophy, spinal muscular atrophy (SMA), spinal-bulbar muscular atrophy (SBMA), progressive bulbar palsy (PBP), post-poliomyelitis syndrome, post-irradiation syndrome, stiff-person syndrome, disorders of the motor units resulting from an accident, myasthenia gravis and Eaton-Lambert syndrome.

Non-FTD amyotrophic lateral sclerosis designates the forms of sporadic or familial amyotrophic lateral sclerosis which are not associated with frontotemporal dementia, and includes amyotrophic lateral sclerosis with parkinsonism-dementia complex 1 (ALS-PDC), familial amyotrophic lateral sclerosis caused by mutation of one of the genes encoding superoxide dismutase 1 (SOD1), TAR DNA binding protein of 43-kDa (TDP-43), RNA-binding protein (FUS/TLS: Fused in Sarcoma/Translocated in Sarcoma) or ubiquilin 2 (UBQLN2). In ALS, patients with bulbar onset progress more rapidly than patients with limb onset or with a LMN presentation. Recent descriptions of regional variants suggest some patients have ALS isolated to a single spinal region, including brachial amyotrophic diplegia, leg amyotrophic diplegia, and isolated bulbar palsy, all of which herein being variants of non-FTD amyotrophic lateral sclerosis. Non-FTD ALS also includes respiratory-onset ALS, a rare variant that accounts for about 3% of all cases of ALS in which the initial symptoms are difficulty breathing with exertion at rest.

Primary lateral sclerosis (PLS) is a type of motor neuron disease that causes nerves within the brain to slowly break down. This makes the nerves unable to activate the motor neurons in the spinal cord, which control muscles.

Hereditary spastic paraplegia (HSP), also known as familial spastic paraparesis (FSP), is caused by upper motor neurons that slowly degenerate causing progressive spasticity and weakness of the legs. This leads to difficulty walking. As degeneration continues, symptoms worsen including impaired vision, ataxia, epilepsy, cognitive impairment, peripheral neuropathy, and/or deafness.

Neurolathyrism is caused by a toxin coming from the consumption of large quantities of certain legumes of the genus *Lathyrus* containing high concentrations of the glutamate analogue neurotoxin β-oxalyl-L-α,β-diaminopropionic acid (ODAP). ODAP is a poison of mitochondria, leading to excess cell death, especially in motor neurons; this toxin causes paralysis, characterized by lack of strength in or inability to move the lower limbs, and may involve pyramidal tracts producing signs of upper motor neuron damage.

Progressive muscular atrophy (PMA) also known as Duchenne-Aran muscular atrophy is clinically characterized by signs of lower motor neuron dysfunction and may evolve into ALS. Symptoms of PMA include atrophy, muscle weakness, lack of reflexes and lack of spasticity, symptoms can be limited to the arms, legs, or both.

Monomelic amyotrophy, also known as benign focal amyotrophy, juvenile segmental atrophy and Hirayama disease, is a rare benign lower motor neuron disorder characterized by muscular weakness and wasting in the distal upper extremities during adolescence followed by a spontaneous halt in progression and a stabilization of symptoms.

Spinal muscular atrophy (SMA) is a disease that deprives people of physical strength by affecting the motor nerve cells in the spinal cord, taking away the ability to walk, eat, or breathe. SMA is caused by a mutation in the survival motor neuron gene 1 (SMN1). that is critical to the function of the nerves that control muscles. Without it, nerve cells cannot properly function and eventually die, leading to debilitating and sometimes fatal muscle weakness.

Spinal-bulbar muscular atrophy (SBMA), also known as bulbospinal muscular atrophy and Kennedy disease, is a genetic disorder in which loss of motor neurons affects voluntary muscle movement, in particular the facial and swallowing muscles, and the arm and leg muscles, particularly those nearest the center of the body.

Progressive bulbar palsy (PBP) involves both upper and lower motor. This form of MND often causes difficulties with speech or swallowing. If the lower motor neurones are affected, the tongue tends to atrophy with visible fasciculation and reduced mobility. This results in a rather nasal type of speech. If the upper motor neurons are affected, the tongue is spastic and tends to cause dysarthria, difficulty with the mechanics of speech.

Stiff-person syndrome, also known as stiff-person spectrum disorder, is a neurological disorder affecting the brain and spinal cord causing fluctuating trunk and limb stiffness, painful muscle spasms, task-specific phobia, an exaggerated startle response, and ankylosing deformities such as fixed lumbar hyperlordosis.

Disorders of the motor units resulting from an accident" as used herein, refers to disorders wherein the motor units have been impaired due to a nerve lesion following an accident, a domestic or a traffic accident for instance.

Myasthenia gravis is an autoimmune disorder that impairs acetylcholine transmission at the neuromuscular junction, i.e. antibodies that attack the acetylcholine receptors resulting in muscle weakness. The most common symptoms of myasthenia gravis are weak, drooping eyelids, Weak eye muscles which cause double vision and excessive weakness of affected muscles after they are used.

Eaton-Lambert syndrome is an autoimmune disease where antibodies interfere with the release of the neurotransmitter acetylcholine receptors at the neuromuscular junction. It causes muscle weakness that tends to begin in the hip and thigh muscles, then typically spreads to the shoulder muscles, and then down the arms and legs to the hands and feet. The nerves that connect the head, face, eyes, nose, muscles, and ears to the brain (cranial nerves) are affected last.

In one embodiment, the sulphate salts of N-(3-(4-(3-(diisobutylamino)propyl)piperazin-1-yl)propyl)-1H-benzo[d]imidazol-2-amine is are those of Formula I Formula I

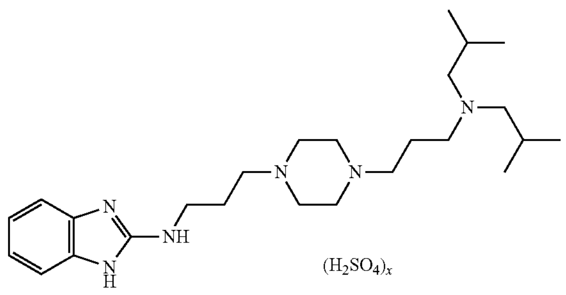

wherein x is 0.5 to 4, preferably x is 0.5 to 3.5, more preferably x is 0.9 to 3.

In other terms, the sulphate salt of N-(3-(4-(3-(diisobutylamino)propyl)piperazin-1-yl)propyl)-1H-benzo[d]imidazol-2-amine contains 0.5 to 4 equivalents, preferably 0.5 to 3.5 equivalents, more preferably 0.9 to 3 equivalents of sulphate for one molecule of N-(3-(4-(3-(diisobutylamino)propyl)piperazin-1-yl)propyl)-1H-benzo[d]imidazol-2-amine.

In one preferred embodiment, x is 1.7 to 2.3, preferably x is 1.9 to 2.1, more preferably x is about 2 or x is 2, In one particularly preferred embodiment, the sulphate salt is N-(3-(4-(3-(diisobutylamino)propyl)piperazin-1-yl)propyl)-1H-benzo[d]imidazol-2-amine di-sulphate.

In one embodiment, the sulphate salt of Formula I is in the form of a pharmaceutically acceptable solvate, preferably a hydrate. The solvate stoichiometry is between 0.5 to 5, preferably between 1 to 4, more preferably between 1.5 to 2.5, still more preferably between 1.8 to 2.2, even more preferably 2 or about 2 molecules of solvate for 1 molecule of sulphate salt of Formula I.

N-(3-(4-(3-(diisobutylamino)propyl)piperazin-1-yl)propyl)-1H-benzo[d]imidazol-2-amine sulphate salts and pharmaceutically acceptable solvates are thus useful as a medicament, in particular for treating or preventing motor neuron diseases, neuromuscular junction disorders and all diseases wherein abnormal translocation of TDP43 from the nucleus to the cytoplasm in motor neurons is observed.

Hence, the invention also concerns a sulphate salt of N-(3-(4-(3-(diisobutylamino)propyl)piperazin-1-yl)propyl)-1H-benzo[d]imidazol-2-amine or a pharmaceutically acceptable solvate thereof as defined herein for use in treating and/or preventing motor neuron diseases and neuromuscular junction disorders, in particular selected from non-FTD amyotrophic lateral sclerosis, primary lateral sclerosis (PLS), hereditary spastic paraplegia (HSP), neurolathyrism, Konzo, Tay-Sachs disease, Sandhoff disease, progressive muscular atrophy (PMA), monomelic amyotrophy, spinal muscular atrophy (SMA), spinal-bulbar muscular atrophy (SBMA), progressive bulbar palsy (PBP), post-poliomyelitis syndrome, post-irradiation syndrome, stiff-person syndrome, disorders of the motor units resulting from an accident, myasthenia gravis, Eaton-Lambert syndrome. Preferably, the disease is selected from non-FTD amyotrophic lateral sclerosis, primary lateral sclerosis (PLS), hereditary spastic paraplegia (HSP), progressive muscular atrophy (PMA), monomelic amyotrophy, spinal muscular atrophy (SMA), spinal-bulbar muscular atrophy (SBMA), progressive bulbar palsy (PBP), myasthenia gravis, Eaton-Lambert syndrome disorders of the motor units resulting from an accident. More preferably, the disease is selected from non-FTD amyotrophic lateral sclerosis, primary lateral sclerosis (PLS), hereditary spastic paraplegia (HSP), spinal muscular atrophy (SMA), spinal-bulbar muscular atrophy (SBMA), progressive bulbar palsy (PBP). Even more preferably, the disease is non-FTD amyotrophic lateral sclerosis.

In other terms, the invention also provides for a method of treating and/or preventing a motor neuron disease or a neuromuscular junction disorder, in particular those cited above as well as embodiments thereof, comprising administering to a patient in need thereof a pharmaceutically effective amount of a N-(3-(4-(3-(diisobutylamino)propyl)piperazin-1-yl)propyl)-1H-benzo[d]imidazol-2-amine sulphate salt or a pharmaceutically acceptable solvate thereof as described herein. In a particular embodiment, the disease is selected from non-FTD amyotrophic lateral sclerosis, primary lateral sclerosis (PLS), hereditary spastic paraplegia (HSP), spinal muscular atrophy (SMA), spinal-bulbar muscular atrophy (SBMA), progressive bulbar palsy (PBP).

In other terms, the invention also provides for the use of N-(3-(4-(3-(diisobutylamino)propyl)piperazin-1-yl)propyl)-1H-benzo[d]imidazol-2-amine sulphate salt or a pharmaceutically acceptable solvate thereof as described herein, in the manufacture of a medicament for treating and/or preventing a motor neuron disease or a neuromuscular junction disorder, in particular those cited above as well as embodiments thereof. In a particular embodiment, the disease is selected from non-FTD amyotrophic lateral sclerosis, primary lateral sclerosis (PLS), hereditary spastic paraplegia (HSP), spinal muscular atrophy (SMA), spinal-bulbar muscular atrophy (SBMA), progressive bulbar palsy (PBP).

In one particular embodiment, the invention also concerns N-(3-(4-(3-(diisobutylamino)propyl)piperazin-1-yl)propyl)-1H-benzo[d]imidazol-2-amine sulphate salt or a pharmaceutically acceptable solvate thereof as defined herein for use in delaying in a patient the onset of motor neuron diseases and neuromuscular junction disorders, in particular selected from non-FTD amyotrophic lateral sclerosis, primary lateral sclerosis (PLS), hereditary spastic paraplegia (HSP), neurolathyrism, Konzo, Tay-Sachs disease, Sandhoff disease, progressive muscular atrophy (PMA), monomelic amyotrophy, spinal muscular atrophy (SMA), spinal-bulbar muscular atrophy (SBMA), progressive bulbar palsy (PBP), post-poliomyelitis syndrome, post-irradiation syndrome, stiff-person syndrome, disorders of the motor units resulting from an accident, myasthenia gravis, Eaton-Lambert syndrome. Preferably, the disease is selected from non-FTD amyotrophic lateral sclerosis, primary lateral sclerosis (PLS), hereditary spastic paraplegia (HSP), progressive muscular atrophy (PMA), monomelic amyotrophy, spinal muscular atrophy (SMA), spinal-bulbar muscular atrophy (SBMA), progressive bulbar palsy (PBP), myasthenia gravis, Eaton-Lambert syndrome, disorders of the motor units resulting from an accident. More preferably, the disease is selected from non-FTD amyotrophic lateral sclerosis, primary lateral sclerosis (PLS), hereditary spastic paraplegia (HSP), spinal muscular atrophy (SMA), spinal-bulbar muscular atrophy (SBMA), progressive bulbar palsy (PBP). Even more preferably, the disease is non-FTD amyotrophic lateral sclerosis.

In other terms, the invention provides for a method for delaying in a patient the onset of motor neuron diseases or neuromuscular junction disorders, in particular those cited above as well as embodiments thereof, comprising administering to a patient in need thereof a pharmaceutically effective amount of a N-(3-(4-(3-(diisobutylamino)propyl)piperazin-1-yl)propyl)-1H-benzo[d]imidazol-2-amine sulphate salt or a pharmaceutically acceptable solvate thereof. In a particular embodiment, the disease is selected from non-FTD amyotrophic lateral sclerosis, primary lateral sclerosis (PLS), hereditary spastic paraplegia (HSP), spinal muscular atrophy (SMA), spinal-bulbar muscular atrophy (SBMA), progressive bulbar palsy (PBP).

In other terms, the invention also provides for the use of N-(3-(4-(3-(diisobutylamino)propyl)piperazin-1-yl)propyl)-1H-benzo[d]imidazol-2-amine sulphate salt or a pharmaceutically acceptable solvate thereof as described herein, in the manufacture of a medicament for delaying in a patient the onset of a motor neuron disease or a neuromuscular junction disorder, in particular those cited above as well as embodiments thereof. In a particular embodiment, the disease is selected from non-FTD amyotrophic lateral sclerosis, primary lateral sclerosis (PLS), hereditary spastic paraplegia (HSP), spinal muscular atrophy (SMA), spinal-bulbar muscular atrophy (SBMA), progressive bulbar palsy (PBP).

According to a further feature of the present invention there is provided a method for reducing abnormal translocation of TDP43 from the nucleus to the cytoplasm in motor neurons, in a patient, preferably a warm blooded animal, and even more preferably a human, in need of such treatment, which comprises administering to said patient an effective amount of N-(3-(4-(3-(diisobutylamino)propyl)piperazin-1-yl)propyl)-1H-benzo[d]imidazol-2-amine sulphate salt or a pharmaceutically acceptable solvate thereof.

According to one embodiment, the sulphate salts of N-(3-(4-(3-(diisobutylamino)propyl)piperazin-1-yl)propyl)-1H-benzo[d]imidazol-2-amine, as well as their pharmaceutical acceptable solvates may be administered as part of a combination therapy. Thus, are included within the scope of the present invention embodiments comprising co-administration of compositions and medicaments which contain, in addition to a sulphate salt of N-(3-(4-(3-(diisobutylamino)propyl)piperazin-1-yl)propyl)-1H-benzo[d]imidazol-2-amine or a pharmaceutically acceptable solvate thereof as active ingredient, additional therapeutic agents and/or active ingredients. Such multiple drug regimens, often referred to as "combination therapy", may be used in the treatment and/or prevention of any motor neuron disease or neuromuscular junction disorder. The use of such combinations of therapeutic agents is especially pertinent with respect to the treatment of the above-mentioned motor neuron diseases within a patient in need of treatment or one at risk of becoming such a patient.

In addition to the requirement of therapeutic efficacy, which may necessitate the use of active agents in addition to the sulphate salts of N-(3-(4-(3-(diisobutylamino)propyl)piperazin-1-yl)propyl)-1H-benzo[d]imidazol-2-amine or pharmaceutically acceptable solvates thereof, there may be additional rationales which compel or highly recommend the use of combinations of drugs involving active ingredients which represent adjunct therapy, i.e., which complement and supplement the function performed by the sulphate salts of N-(3-(4-(3-(diisobutylamino)propyl)piperazin-1-yl)propyl)-1H-benzo[d]imidazol-2-amine or pharmaceutically acceptable solvates thereof. Suitable supplementary therapeutic agents used for the purpose of auxiliary treatment include drugs which, instead of directly treating and/or preventing a disease or condition mediated by or associated with motor neuron degeneration, neuromuscular junction degeneration and/or pathological accumulation of TDP-43 in the cytoplasm of motor neurons, treat diseases or conditions which directly result from or indirectly accompany said degenerations.

According to a further feature of the present invention, a succinate salt of N-(3-(4-(3-(diisobutylamino)propyl)piperazin-1-yl)propyl)-1H-benzo[d]imidazol-2-amine, a pharmaceutically acceptable solvate thereof may be used in combination therapy with other drugs used for treating motor neuron diseases such as ALS, SMA, SBMA and neuromuscular junction disorders such as myasthenia gravis and Eaton-Lambert syndrome. More particularly, the compound of Formula I, as well as pharmaceutically acceptable solvates thereof, may be used as an adjunct therapy in combination with riluzole, edavarone, pyridostigmine, inhibitors of glucosylceramide degradation such as ambroxol and conduritol B epoxide, acetylcholine release inducers such as guanidine, corticosteroids such as prednisolone, antiseizure drugs such as carbamazepine and phenytoin, or drugs that are currently under clinical trial for the treatment of ALS as disclosed in Van Eijk et al., *Current opinion in neurology* 2020, 33(5), 655.

Thus, the methods of treatment and pharmaceutical compositions of the present invention may employ a N-(3-(4-(3-(diisobutylamino)propyl)piperazin-1-yl)propyl)-1H-benzo[d]imidazol-2-amine or a pharmaceutically acceptable solvate thereof in monotherapy of motor neuron diseases and neuromuscular junction disorders. However, said methods and compositions may also be used multiple therapy in which one or more N-(3-(4-(3-(diisobutylamino)propyl)piperazin-1-yl)propyl)-1H-benzo[d]imidazol-2-amine or their pharmaceutically acceptable salts or solvates are co-administered in combination with one or more other therapeutic agents.

In the above-described embodiment, combinations of N-(3-(4-(3-(diisobutylamino)propyl)piperazin-1-yl)propyl)-1H-benzo[d]imidazol-2-amine or a pharmaceutically acceptable salt or solvate thereof and other therapeutic active agents may be administered, in terms of dosage forms, either separately or in conjunction with each other, and in terms of their time of administration, either serially or simultaneously. Thus, the administration of one component agent may be prior to, concurrent with, or subsequent to the administration of the other component agent(s).

Generally, for pharmaceutical use, the sulphate salts of N-(3-(4-(3-(diisobutylamino)propyl)piperazin-1-yl)propyl)-1H-benzo[d]imidazol-2-amine or pharmaceutically acceptable solvates thereof may be formulated as a pharmaceutical composition comprising at least one sulphate salt of N-(3-(4-(3-(diisobutylamino)propyl)piperazin-1-yl)propyl)-1H-benzo[d]imidazol-2-amine or a pharmaceutically acceptable solvate thereof and at least one pharmaceutically acceptable carrier, diluent, excipient and/or adjuvant, and optionally one or more further therapeutic agents and/or active ingredients.

By means of non-limiting examples, pharmaceutical composition may be in a dosage form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences. The pharmaceutical compositions may be formulated in solid form and re-dissolved or suspended prior to use.

Some preferred, but non-limiting examples of dosage forms include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, agar, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The pharmaceutical compositions can optionally contain other substances that are commonly used in pharmaceutical formulations, such as lubricating agents, wetting agents, emulsifying and suspending agents, dispersing agents, disintegrating agents, stabilizing agents, isotonic agents, bulking agents, fillers, preserving agents, sweetening agents, flavouring agents, perfuming agents, colouring agents, antibacterial agents and/or antifungal agents such as parabens, chlorobutanol, phenol, sorbic acid, dispensing agents, flow regulators, release agents, etc. The compositions may also be formulated so as to provide rapid, sustained or delayed release of the active compound(s) contained therein.

The pharmaceutical compositions of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, of the at least one compound of the invention, e.g. about 10, 25, 50, 100, 200, 300 or 400 mg per unit dosage.

Usually, depending on the condition to be prevented or treated and the route of administration, the active compound of the invention will usually be administered between 0.01 to 100 mg per kilogram, more often between 0.1 and 50 mg, such as between 1 and 25 mg, for example about 0.5, 1, 2, 5, 10, 15, 20 or 25 mg, per kilogram body weight of the patient per day, which may be administered as a single daily dose, divided over one or more daily doses, or essentially continuously, e.g. using a drip infusion.

All references to compounds of Formula I include references to solvates, in particular hydrates, multi-component complexes and liquid crystals thereof.

The compounds disclosed throughout the present application were named using ChemDraw® Ultra version 11.0 (CambridgeSoft, Cambridge, MA, USA).

N-(3-(4-(3-(diisobutylamino)propyl)piperazin-1-yl)propyl)-1H-benzo[d]imidazol-2-amine free base can be obtained as disclosed in WO 2006/051489, its sulphate salts and solvates thereof were prepared according to the procedures reported in WO 2014/102339.

Definitions

The definitions and explanations below are for the terms as used throughout the entire application, including both the specification, the figures and the claims.

The term "administration", or a variant thereof (e.g., "administering"), means providing the active agent or active ingredient (e.g. N-(3-(4-(3-(diisobutylamino)propyl)piperazin-1-yl)propyl)-1H-benzo[d]imidazol-2-amine), alone or as part of a pharmaceutically acceptable composition, to the patient in whom/which the condition, symptom, or disease is to be treated or prevented.

The term "human" refers to a subject of both genders and at any stage of development (i.e. neonate, infant, juvenile, adolescent, adult).

The term "patient" refers to a warm-blooded animal, more preferably a human, who/which is awaiting the receipt of, or is receiving medical care or is/will be the object of a medical procedure.

By "pharmaceutically acceptable" is meant that the ingredients of a pharmaceutical composition are compatible with each other and not deleterious to the patient thereof.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The expression "reducing" as used herein refers to a partial reduction or a complete reduction.

The term "solvate" is used herein to describe a compound in this invention that contains stoichiometric or sub-stoichiometric amounts of one or more pharmaceutically acceptable solvent molecule such as ethanol. The term "hydrate" is employed when said solvent is water. The pharmaceutically acceptable solvent molecules may be co-crystallized with the compound of the invention, and/or be present in crystalline and/or amorphous phases of solids thereof, and/or be adsorbed thereto.

The term "therapeutically effective amount" (or more simply an "effective amount") as used herein means the amount of active agent or active ingredient (e.g. N-(3-(4-(3-(diisobutylamino)propyl)piperazin-1-yl)propyl)-1H-benzo[d]imidazol-2-amine) that is sufficient to achieve the desired therapeutic or prophylactic effect in the patient to which/whom it is administered.

The terms "treat", "treating" and "treatment, as used herein, are meant to include alleviating, attenuating or abrogating a condition or disease and/or its attendant symptoms.

The present invention will be better understood with reference to the following examples. These examples are intended to representative of specific embodiments of the invention, and are not intended as limiting the scope of the invention.

BIOLOGY EXAMPLES

Figure 1:
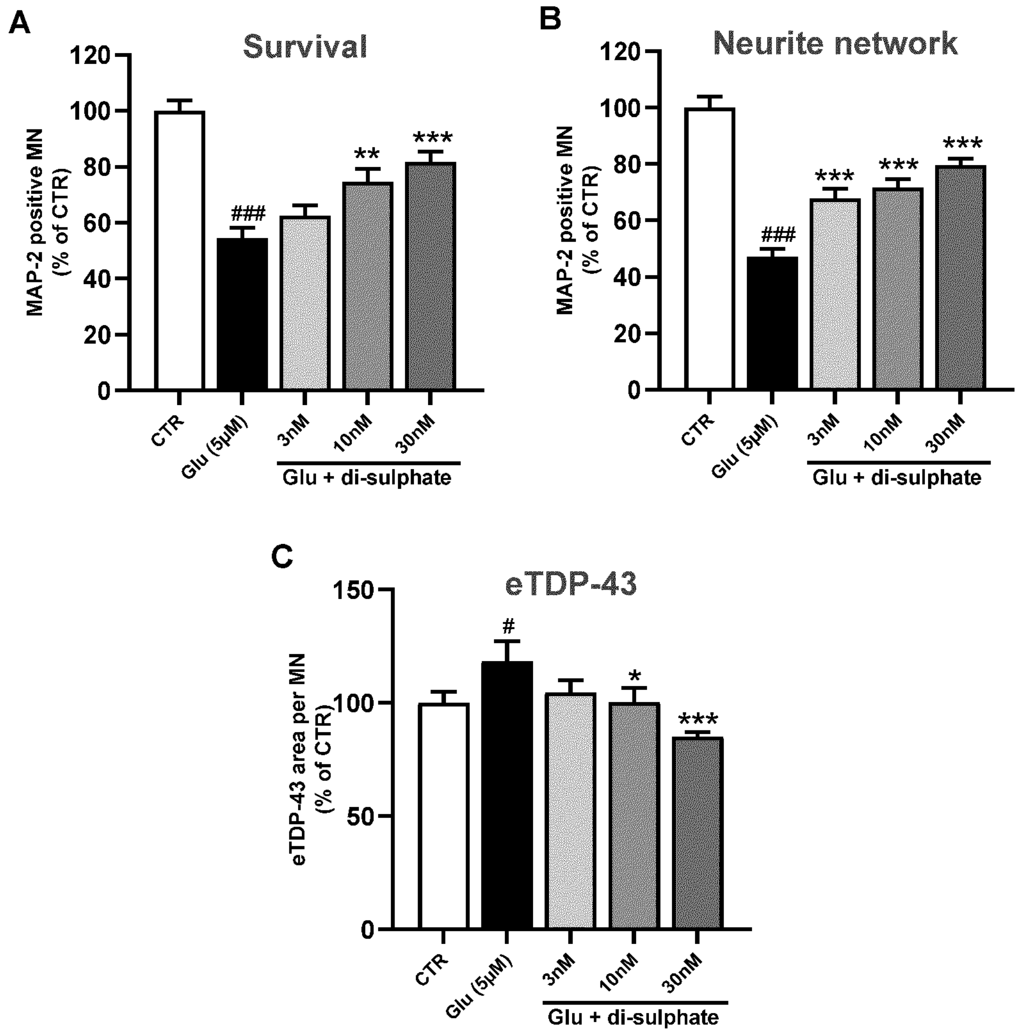
FIG. 1 shows the effect of an incubation of N-(3-(4-(3-(diisobutylamino)propyl)piperazin-1-yl)propyl)-1H-benzo[d]imidazol-2-amine) di-sulphate for 48 h after 20 min of glutamate injury, in a primary culture of rat spinal motor neurons on survival (A), neurite network (B) and on extra-nuclear TDP-43 (eTDP43) (C) of MAP-2 positive MNs. Results are expressed as a percentage of control as mean±SEM (n=5-6/group). One-way ANOVA followed by PLSD Fisher's test.

Example 1: effect of N-(3-(4-(3-(diisobutylamino)propyl)piperazin-1-yl)propyl)-1H-benzo[d]imidazol-2-amine) di-sulphate on rat primary motor neurons injured with glutamate Culture of Primary Motor Neurons Rat motor neurons (MN) were cultured as previously described by Martinou et al., *Neuron.* 1992, April; 8(4), 737-44 and Wang et al. *Hum. Mol. Genet.,* 2013 Dec. 1; 22(23), 4706-19. Pregnant female rats of 14 days gestation (Rats Wistar; Janvier Labs France) were killed using a deep anesthesia with $CO_2$ followed by cervical dislocation. Then, fetuses were removed from the uterus and immediately placed in ice-cold L15 Leibovitz medium with a 2% penicillin (10,000 U/mL) and streptomycin (10 mg/mL) solution (PS) and 1% bovine serum albumin (BSA). Spinal cords were treated for 20 min at 37° C. with a trypsin-Ethylenediaminetetraacetic acid (EDTA) solution at a final concentration of 0.05% trypsin and 0.02% EDTA. The dissociation was stopped by the addition of Dulbecco's modified Eagle's medium (DMEM) with 4.5 g/liter of glucose, containing DNAse I grade II (final concentration 0.5 mg/mL) and 10% fetal calf serum (FCS). Cells were mechanically dissociated by three forced passages through the tip of a 10-mM pipette. Cells were then centrifuged at 180×g for 10 min at +4° C. on a layer of BSA (3.5%) in L15 medium. The supernatant was discarded, and the pellet was resuspended in a defined culture medium consisting of Neurobasal medium with a 2% solution of B27 supplement, 2 mmol/liter of L-glutamine, 2% of PS solution, and 10 ng/mL of brain-derived neurotrophic factor (BDNF). Viable cells were counted in a Neubauer cytometer, using the trypan blue exclusion test. The cells were seeded at a density of 20,000 per well in 96-well plates (immunostaining) precoated with poly-L-lysine and cultured at 37° C. in an air (95%)-$CO_2$ (5%) incubator. The medium was changed every 2 days. The motor neurons were injured with glutamate after 13 days of culture.

Compound Treatment

On day 13 of culture, glutamate was added to a final concentration of 5 μM diluted in control medium in presence of the sulphate salt for 20 min. After 20 min, glutamate was washed and fresh culture medium with the sulphate salt was added for 48 hours.

Endpoint Evaluation—48 h Co-Incubation

After 14 or 15 days of culture (48 h after the glutamate injury), the cell culture supernatant was collected and the spinal cord MNs were fixed by a cold solution of ethanol (95%) and acetic acid (5%) for 5 min at −20° C. After permeabilization with 0.1% of saponin, cells were blocked for 2 h with PBS containing 1% fetal calf serum. Then, cells were incubated with:

a) mouse monoclonal antibody anti-microtubule associated protein 2 (MAP-2) at dilution of 1/400 in PBS containing 1% fetal calf serum and 0.1% of saponin. This antibody binds specifically MAP-2 present in cell bodies and neurites of all MNs. This antibody was revealed with Alexa Fluor 488 goat anti-mouse IgG. Nuclei of neurons were labeled by a fluorescent marker (Hoechst solution).

b) Rabbit polyclonal antibody anti-TDP43 at dilution of 1/100 in PBS containing 1% fetal calf serum and 0.1% of saponin. Cytoplasmic localization of TDP43 was investigated.

This antibody was revealed with Alexa Fluor 568 goat anti-rabbit IgG For each condition, 30 pictures (representative of 90% of the well area) per well were automatically taken using ImageXpress (Molecular Devices) with 20× magnification. All images were taken under the same conditions (exposition time, gain and laser intensity). Analysis of different endpoints, were automatically performed using Custom Module Editor (Molecular Devices). Motoneurons (MAP-2) were distinguished from interneurons (staining MAP-2) using the following morphological criteria: a cell body diameter >15 mm and the presence of a minimum of three neuritic processes (Ferraiuolo et al. *Brain* 2011: 134; 2627-2641).

The endpoints were:

survival of MN (number of MN)

total neurite outgrowth of MN (expressed in μm)

TDP43 (extranuclear, eTDP43) in MN (expressed as area eTDP43-$\mu m^2$/number of MN)

Statistical Analysis

All values are expressed as mean+/−SEM. Statistical analysis was performed by one-way ANOVA, followed by PLSD Fisher test. Neuro-Sys performed graphs and statistical analyses on the different conditions, using GraphPad Prism software version 7.04. *$p<0.05$ was considered significant.

Results

Motor neuron survival: as expected, the glutamate intoxication significantly decreased cell survival, as compared to the control group (mean survival: 55%; FIG. 1A). Low doses of N-(3-(4-(3-(diisobutylamino)propyl)piperazin-1-yl)propyl)-1H-benzo[d]imidazol-2-amine) di-sulphate (10 nM to 30 nM) showed a positive and significant effect on survival, as compared to the glutamate condition. The maximal effect was obtained with the dose at 30 nM (mean survival: 82%).

Neurite network integrity: glutamate significantly reduced the neurite network (FIG. 1B). All investigated doses of N-(3-(4-(3-(diisobutylamino)propyl)piperazin-1-yl)propyl)-1H-benzo[d]imidazol-2-amine) di-sulphate application were able to improve the neurite network after glutamate injury, with a maximal effect at 30 nM (mean length: 80%).

Extranuclear TDP-43: glutamate application significantly increased abnormal cytoplasmic TDP-43 signal (FIG. 1C). The di-sulphate salt at concentrations of 10, and 30 nM was able to prevent the accumulation of TDP-43 in the cytoplasm.

Example 2: effect of N-(3-(4-(3-(diisobutylamino)propyl)piperazin-1-yl)propyl)-1H-benzo[d]imidazol-2-amine) di-sulphate pre-treatment on rat primary motor neurons injured with glutamate 24 h pre-treatment-injury-24 h treatment Culture of Primary Motor Neurons The culture was carried out as described in example 1.

Compound Treatment—24 h Pre-Incubation+24 h Co-Incubation

On day 12 of culture, primary motor neurons were treated with the sulphate salt for 24 hours. On day 13 of culture, glutamate was added to a final concentration of 5 μM diluted in control medium in presence of the sulphate salt for 20 min. After 20 min, glutamate was washed and fresh culture medium with the sulphate salt was added for an additional 24 hours.

End Point Evaluation

The end point evaluation was carried out as described in example 1.

Statistical Analysis

The statistical analysis was carried out as described in example 1.

Results

Figure 2:
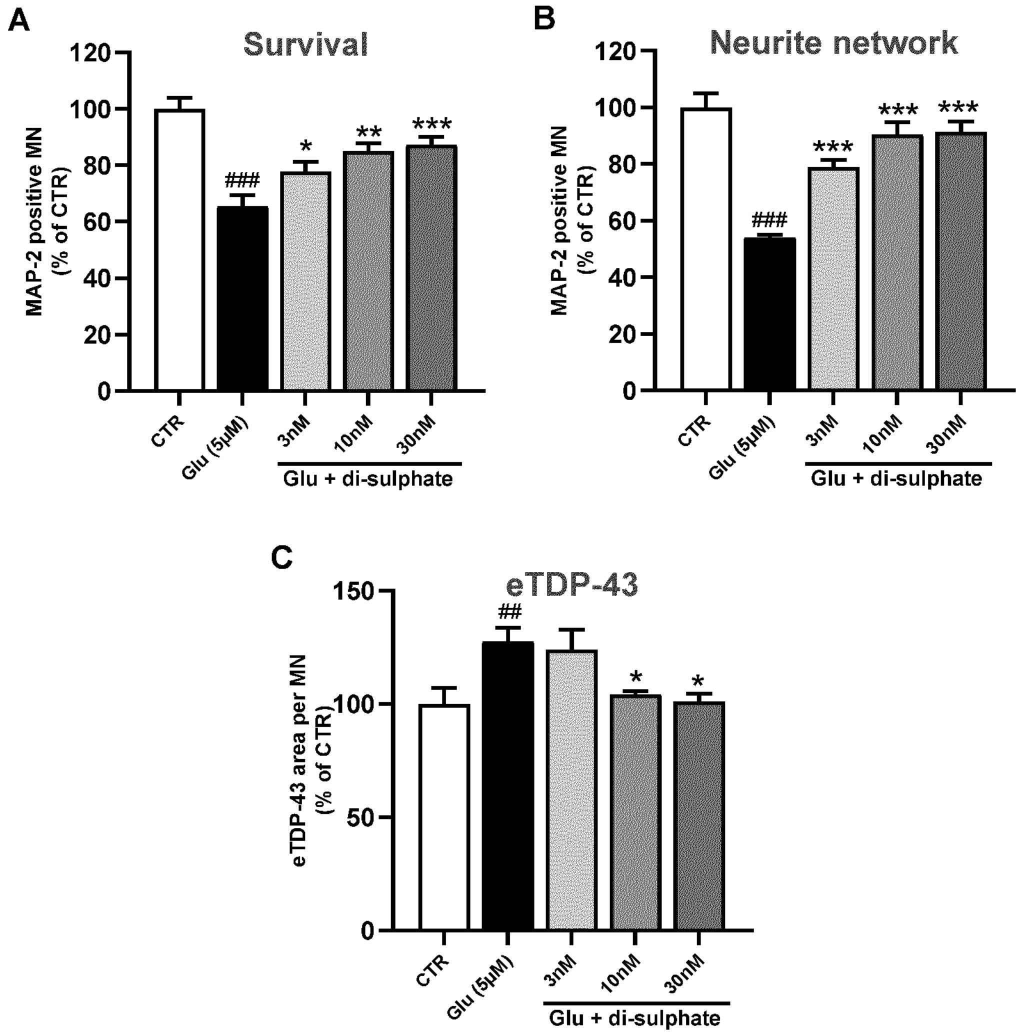
FIG. 2 shows the effect of a 24 h pre-incubation of N-(3-(4-(3-(diisobutylamino)propyl)piperazin-1-yl)propyl)-1H-benzo[d]imidazol-2-amine) di-sulphate before 20 min of glutamate injury plus 24 h post-injury incubation, on survival (A), neurite network (B) and on extra-nuclear TDP-43 (eTDP43) (C) of MAP-2 positive MNs. Results are expressed as a percentage of control as mean±SEM (n=5-6/group). One-way ANOVA followed by PLSD Fisher's test.

Motor neuron survival: as expected, glutamate significantly decreased cell survival, as compared to the control group (mean survival: 65%; FIG. 2A). Low doses of the sulphate salt (3 nM to 30 nM) displayed positive and significant effect on survival, as compared to the glutamate condition. The maximal effect was obtained with the dose of sulphate salt at 30 nM (mean survival: 87%).

Neurite network integrity: glutamate strongly impaired the neurite network of spinal motor neurons (FIG. 1B). All investigated doses of the sulphate salt were able to protect the neurite network from glutamate damage, with a maximal effect at 30 nM (mean length: 91%).

Extranuclear TDP-43: glutamate application significantly increased cytoplasmic TDP43 signal (mean eTDP-43 signal: 128% compared to control, FIG. 1C). The sulphate salt (at the doses of 10 nM to 30 nM) were also able to fully prevent the abnormal distribution of TDP-43.

Example 3: effect of N-(3-(4-(3-(diisobutylamino)propyl)piperazin-1-yl)propyl)-1H-benzo[d]imidazol-2-amine) di-sulphate on rat primary SOD1 motor neuron maturation after a glutamate injury Genetic rodent models have been used to study ALS pathogenesis, including rats over-expressing human superoxide dismutase 1 (SOD1) with mutations known to cause human familial ALS (eg. SOD1G93A rats). The ALS rat model expressing the mutated form of hSOD-1G93A exhibits features that closely recapitulate the clinical and histopathologic features of the human disease (Nagai et al., *The Journal of Neuroscience*, Dec. 1, 2001, 21(23):9246-9254). In human or rodent studies (SOD1 models), MN loss is preceded by increased excitability. As increased neuronal excitability correlates with structural changes in dendritic arbors and spines, dendritic atrophy and spine loss in striatal medium spiny neurons (MSNs) and lower MNs of lumbar spinal cord are observed (Ferrucci et al., *Neurobiology of Disease* 37 (2010) 370-383; Avossa et al., *Neuroscience* 138 (2006) 1179-1194).

Genotyping of Embryos for SOD1 Motoneurons

The day of the dissection (from pregnant females at 14 days of gestation), a piece of each embryo head (~3 $mm^3$) was placed in a 2 mL tube free DNase with a new scalpel. The DNA was extracted with the SYBR Green Extract-N-Amp tissue PCR kit (Sigma Aldrich). Briefly, 120 μL of extraction solution was put on each piece of embryo heads. Then, they were incubated for 10 min at room temperature. At the end of this incubation period, the heads were incubated for 5 min at 95° C. Immediately after this last incubation, 100 μL of neutralizing solution was added; each DNA extract was diluted at 1/40 and stored at +4° C. until use. $SOD1^{G93A}$ gene was determined using genomic fragment with human SOD1 primers (5'-CATCAGCCCTAATCCATCTGA-3'; 5'-CGCGACTAACAATCAAAGTGA-3'). The SOD1 primers were diluted at 3 μM in sterile ultrapure water. Briefly, a mix for PCR was prepared with ultrapure water (4 μL per sample), primer at 3 μM (2 μL per sample) and Master Mix (10 μL per sample). In a PCR 96 wells plate, 16 μL of PCR mix was added in each well. 4 μL of each diluted DNA was added according to a plan deposit.

The RT-PCR was run using the CFX96 Biorad RT-PCR system, using the following program:

beginning: 95° C.—20 sec 45 cycles: 95° C.—10 sec, 65° C.—10 sec, 72° C.—30 sec (data acquisition)

melt curve: 95° C.—15 sec, 64° C.—1 min, 90° C.—30 sec (continuous data acquisition), 60° C. 15 sec The amplification plots and melt curves were analyzed thanks to the Biorad software. The results for each sample were compared to negative control (ultrapure water) and to the positive control, to conclude on the genotype of each embryo (WT or Tg).

Culture of Spinal Cord SOD1 Motor Neurons

Rat spinal cord (SC) motor neurons were cultured as described by Martinou et al., *Neuron.* 1992, April; 8(4), 737-44 and Wang et al. *Hum. Mol. Genet.,* 2013 Dec. 1; 22(23), 4706-19. Pregnant female rats of 14 days of gestation were killed by cervical dislocation. Fetuses were collected and immediately placed in ice-cold L15 Leibovitz medium with a 2% penicillin (10,000 U/mL) and streptomycin (10 mg/mL) solution (PS) and 1% bovine serum albumin (BSA). Each fetus was dispatched on numerating petri dish (35 mm of diameter). Tail of fetuses were cut, placed on 1.5 ml tube free DNAase; the DNA was extracted with the Extract-N-Amp Tissue Kit.

The genotyping of SOD tg fetuses was performed with the kit Fast SYBR Green Master Mix. This genotyping was made during the dissection of spinal cord, thus at the end of the dissection culture of SOD Tg spinal cord and WT spinal cord was done. Spinal cords were removed and placed in ice-cold medium of Leibovitz (L15).

SC were treated for 20 min at 37° C. with a trypsin-EDTA solution at a final concentration of 0.05% trypsin and 0.02% EDTA. The dissociation was stopped by addition of Dulbecco's modified Eagle's medium (DMEM) with 4.5 g/liter of glucose, containing DNAse I grade II (final concentration 0.5 mg/mL) and 10% fetal calf serum (FCS). Cells were mechanically dissociated by three forced passages through the tip of a 10-ml pipette. Cells were then centrifuged at 180×g for 10 min at +4° C. on a layer of BSA (3.5%) in L15 medium. The supernatant was discarded, and the pellet was resuspended in a defined culture medium consisting of Neurobasal medium with a 2% solution of B27 supplement, 2 mmol/liter of L glutamine, 2% of PS solution, and 10 ng/mL of brain-derived neurotrophic factor (BDNF). Viable cells were counted in a Neubauer cytometer, using the trypan blue exclusion test. The cells were seeded at a density of 20,000 per well in 96-well plates (immunostaining) precoated with poly-L-lysine and were cultured at 37° C. in an air (95%)-$CO_2$ (5%) incubator. The medium was changed every 2 days.

Compound Treatment—48 h Co-Incubation

On day 13, medium was removed and cultures were exposed to the test compounds: N-(3-(4-(3-(diisobutylamino)propyl)piperazin-1-yl)propyl)-1H-benzo[d]imidazol-2-amine) di-sulphate, in comparison to Riluzole and Edavarone, and glutamate (5 μM) for 20 min at 37° C. in defined medium. After glutamate exposure, the cultures were washed with defined medium at 37° C. then placed in fresh culture medium containing the test compound for additional 48 h.

End Point Evaluation

After 15 days of culture (48 hours after the glutamate injury), the cell culture supernatant was taken off and the spinal cord motor neurons were fixed by a cold solution of ethanol (95%) and acetic acid (5%) for 5 min at −20° C.

After permeabilization with 0.1% of saponin, cells were incubated for 2 hours with:

- a mouse monoclonal antibody anti microtubule-associated-protein 2 (MAP-2) at dilution of 1/400 in PBS containing 1% fetal calf serum and 0.1% of saponin (this antibody stains all motor neurons, mature and early differentiated), this antibody will be revealed with Alexa Fluor 488 goat anti-mouse IgG.
- a rabbit polyclonal antibody anti-TDP-43, at a dilution of 1/100, in PBS containing 1% fetal calf serum and 0.1% of saponin (this antibody binds to TDP43, a protein subjected to abnormal translocation in ALS). TDP-43 (nuclear and cytoplasmic) was taken into consideration. This antibody was revealed with Alexa Fluor 568 goat anti-rabbit IgG. Nuclei of neurons will be labeled by a fluorescent marker (Hoechst solution).

The endpoints were:

total survival of MN (number of MAP-2 positive MNs), total neurite network (length expressed in μm) of MAP-2 positive neurites, cytoplasmic TDP43 (extranuclear, eTDP-43) in MNs expressed as area ($\mu m^2$)/number of MNs.

Statistical Analysis

The statistical analysis was carried out as described in example 1.

Results

Figure 3:
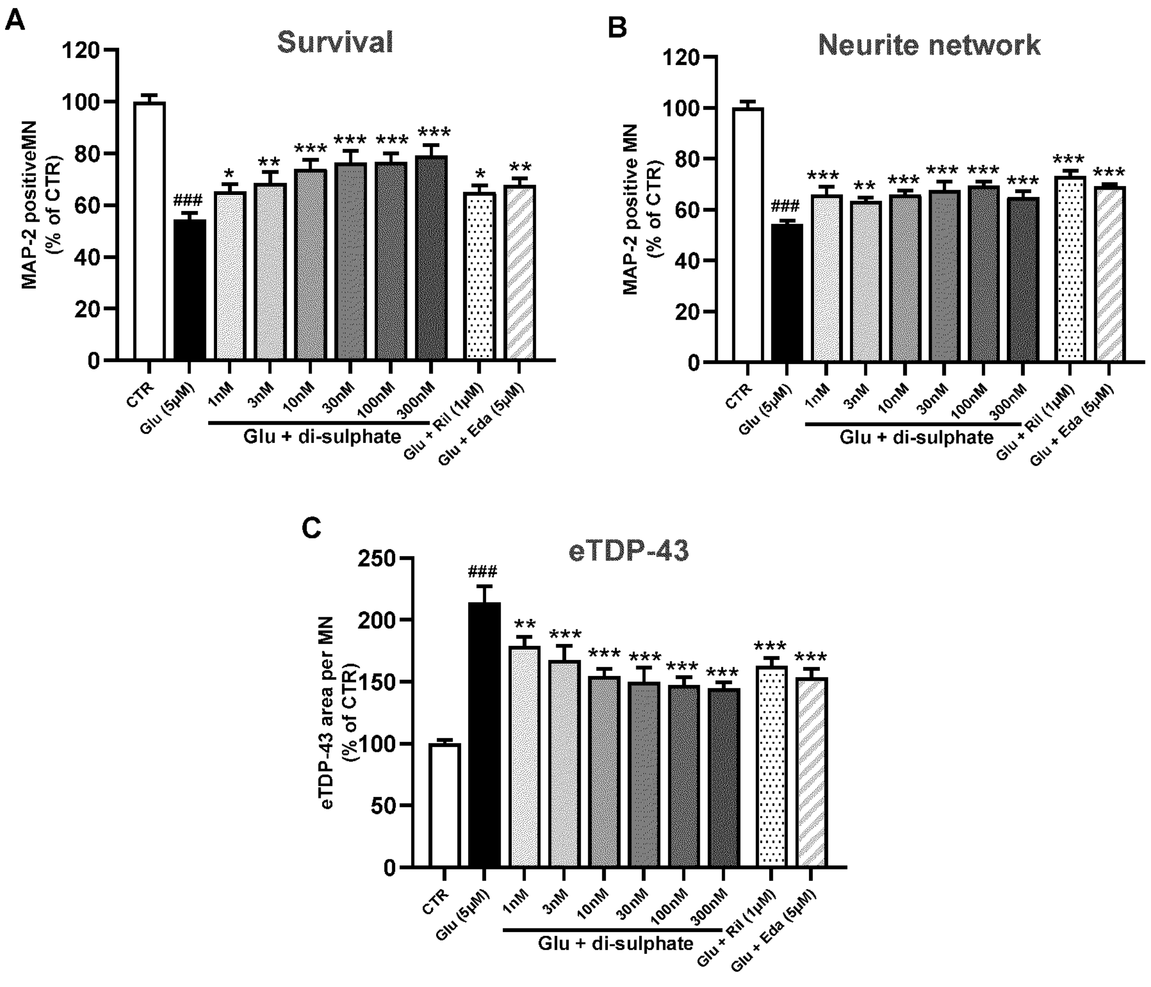
FIG. 3 shows the effects of N-(3-(4-(3-(diisobutylamino)propyl)piperazin-1-yl)propyl)-1H-benzo[d]imidazol-2-amine) di-sulphate, in comparison to Riluzole (Ril) and Edavarone (Eda), in a primary culture of $SOD1^{G93A}$ Tg rat spinal cord motor neurons injured with glutamate. (A) Number of neurons (A), integrity of the neurite network (B) and translocation of TDP43 (C). Results are expressed as a percentage of control as mean+/−SEM (n=4-6). One-way ANOVA followed by PLSD Fisher's test.
Figure 4:
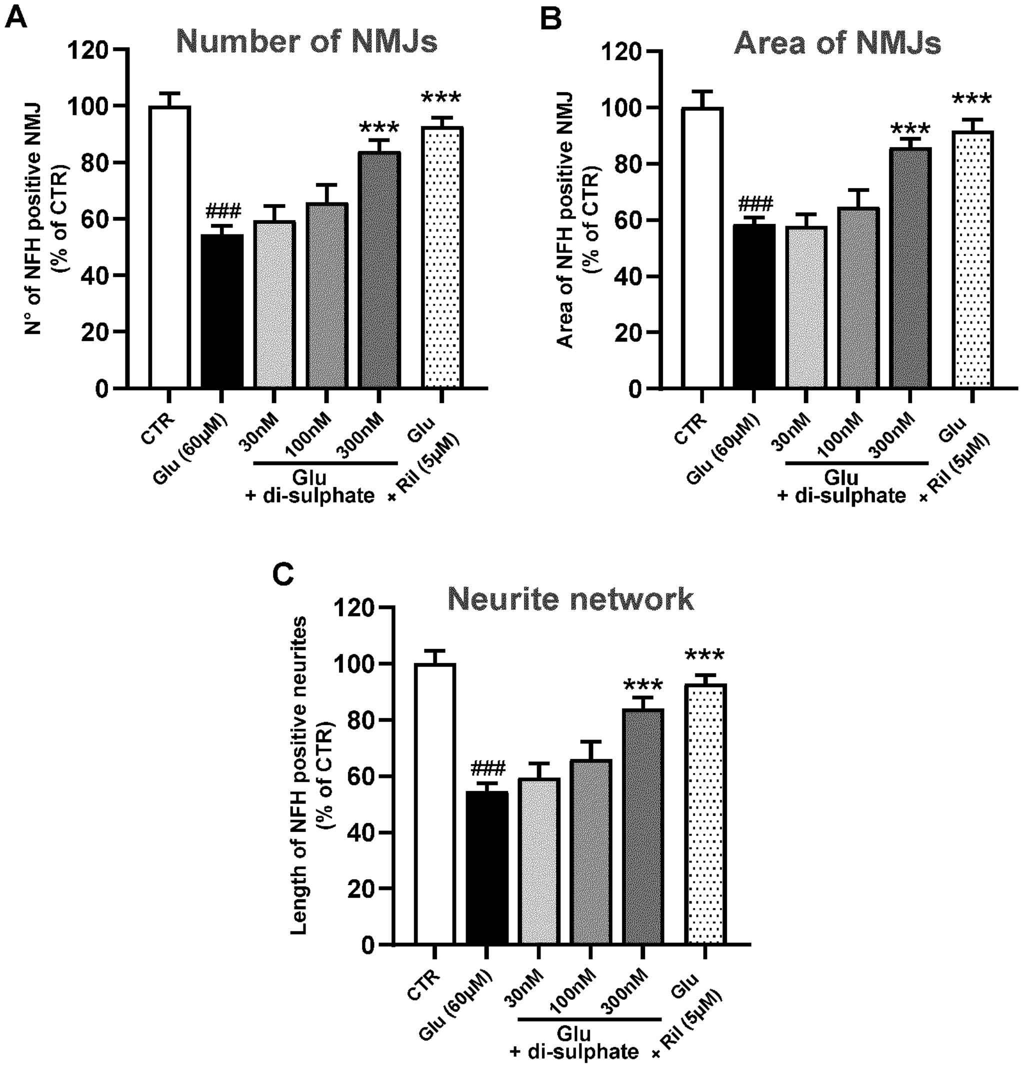
FIG. 4 shows the effect of N-(3-(4-(3-(diisobutylamino)propyl)piperazin-1-yl)propyl)-1H-benzo[d]imidazol-2-amine) di-sulphate, in comparison to Riluzone (Ril) in a coculture of spinal cord explant and myoblasts injured by glutamate: (A) number of NMJs, (B) size of NMJs, and (C) neurite network of NFH (+) MN. Results are expressed as a percentage of control as mean+/−SEM (n=4-6). One-way ANOVA followed by PLSD Fisher's test.

The application of glutamate significantly reduced the number of MNs, reduced the length of their neurite network and triggered an abnormal distribution of TDP-43 towards the cytoplasm (see FIG. 3).

All investigated doses of N-(3-(4-(3-(diisobutylamino)propyl)piperazin-1-yl)propyl)-1H-benzo[d]imidazol-2-amine) di-sulphate were neuroprotective. The protective effects on neuronal survival and on the distribution of TDP-43 were dose-dependent. At a dose of 300 nM, the protective effects of N-(3-(4-(3-(diisobutylamino)propyl)piperazin-1-yl)propyl)-1H-benzo[d]imidazol-2-amine) di-sulphate were greater than those of Riluzole or Edaravone even at higher 1 μM and 5 μM concentrations respectively.

Example 4: effect of N-(3-(4-(3-(diisobutylamino)propyl)piperazin-1-yl)propyl)-1H-benzo[d]imidazol-2-amine) di-sulphate on spinal cord/muscle neuromuscular junctions injured with glutamate Culture of Human Myoblasts and Rat Spinal Cord Explants All experiments were carried out in accordance with the National Institutes of Health Guide for the Care and Use of Laboratory Animals and followed current European Union regulations (Directive 2010/63/EU).

The human muscle cell line was established from dissociated cells (22 000 cells per wells). They were plated in gelatin-coated 0.1% in water on 48 wells plate and were allowed to grow in a proliferation medium consisting of mix of 62% of MEM medium and 25% of M199 medium supplemented with glutamine 2 mM, human insulin 10 µg/mL, human recombinant epidermal growth factor 10 ng/mL (EGF), human recombinant fibroblast growth factor basic 2 ng/mL (bFGF), fetal calf serum 10% (FCS) and 2% of penicillin 10.000 U/mL and streptomycin 10.000 µg/mL (PS). The medium will be changed every 2 days.

Five days after the start of culture, immediately after the fusion of satellite cells, whole transverse slices of spinal cords with 4 dorsal root ganglia (DRG) attached, taken from 13-day-old rat Wistar embryos (Janvier Labs, France), were placed on the muscle monolayer (one explant per well in the central area). The presence of DRG are necessary to achieve a good ratio of innervation. Innervated cultures were maintained in a mixed (67%/25%) medium composed of MEM and medium 199, supplemented with 5% FCS, insulin 5 µg/ml, glutamine 2 mM and 2% PS. After 24 h of co-culture, neurite elongation from spinal cord explants is usually observed. These neurites made contacts with myotubes and induced the formation of neuromuscular junctions and the first contractions were observed after ~8 days of co-culture. Quickly thereafter, innervated muscle fibers located in the proximity to the spinal cord explants, were virtually continuously contracting. Innervated fibers were morphologically and spatially distinct from the non-innervated ones and could easily be distinguished from them. The plates were maintained at 37° C. in a humidified incubator, in an atmosphere of air (95%)-$CO_2$ (5%).

Compound Treatment—48 h Co-Incubation

On day 27 (co-culture), co-cultures were incubated with N-(3-(4-(3-(diisobutylamino)propyl)piperazin-1-yl)propyl)-1H-benzo[d]imidazol-2-amine) di-sulphate and glutamate application. Glutamate was added to a final concentration of 60 µM diluted in control medium, in presence of the di-sulphate salt for 20 min.

After 20 min intoxication, the supernatant was removed and fresh culture medium with N-(3-(4-(3-(diisobutylamino)propyl)piperazin-1-yl)propyl)-1H-benzo[d]imidazol-2-amine) di-sulphate was added for an additional 48 h.

End Point Evaluation

Immunostaining

After 48 hours of intoxication, cells were incubated with 500 nM α-bungarotoxin coupled with Alexa 488 during 15 min in the culture medium at 37° C. to detect motor endplates. After 2 washing in PBS, cells were fixed by a solution of 4% of paraformaldehyde in PBS, pH=7.3 for 20 min at room temperature.

The cells were washed twice in PBS. A solution of PBS containing 0.1% of saponin and 1% FCS for 15 min at room temperature to permeabilized cells and block non-specific sites.

Then, co-cultures were incubated with a mouse monoclonal anti-neurofilament 200 KD antibody (NFH) at the dilution of 1/400 in PBS containing 1% FCS, 0.1% saponin, for 2 h at room temperature. Antibody against NFH stained neurites and the axon of motor neuron. This antibody was revealed with Alexa Fluor 568 goat anti-mouse IgG at the dilution 1/400 in PBS containing 1% FCS, 0.1% saponin, for 1 h at room temperature. Nuclei of neurons were labeled by Hoechst solution, a nuclear fluorescent marker at 1 µm/ml in the same solution.

Analysis

One co-culture was done (6 wells per conditions). For each condition, 20 pictures per well were automatically taken using ImageXpress (Molecular devices) with 10× magnification. All the images were taken under the same conditions.

The following endpoints were automatically measured:

(1) number of NMJs, (2) mean size of NMJs (NMJ area in µm$^2$), (3) total neurite length (µm) (=innervation network).

Statistical Analysis

The statistical analysis was carried out as described in example 1.

Results

The application of glutamate (60 µM, 20 min) resulted in a significant reduction in the number (A) and the total area (B) of NMJs in the culture. In addition, the injury led to a significant loss of neurite (C). The di-sulphate salt (300 nM) displayed neuroprotective effects, on a dose-dependent manner, as it increased the number, the total area of NMJs and the total neurite network, it successfully protected the neuromuscular junctions and the neurite network against the glutamatergic stress.

The invention claimed is:

1. A method for treating motor neuron diseases and neuromuscular junction disorders selected from non-FTD amyotrophic lateral sclerosis, primary lateral sclerosis (PLS), hereditary spastic paraplegia (HSP), neurolathyrism, Konzo, Tay-Sachs disease, Sandhoff disease, progressive muscular atrophy (PMA), monomelic amyotrophy, spinal muscular atrophy (SMA), spinal-bulbar muscular atrophy (SBMA), progressive bulbar palsy (PBP), post-poliomyelitis syndrome, post-irradiation syndrome, stiff-person syndrome, disorders of the motor units resulting from an accident, myasthenia gravis, and Eaton-Lambert syndrome, comprising administering to a patient in need thereof an effective amount of a sulphate salt of N-(3-(4-(3-(diisobutylamino) propyl) piperazin-1-yl) propyl)-1H-benzo[d]imidazol-2-amine and pharmaceutically acceptable solvates thereof.

2. A method for delaying in a patient the onset of motor neuron diseases and neuromuscular junction disorders selected from non-FTD amyotrophic lateral sclerosis, primary lateral sclerosis (PLS), hereditary spastic paraplegia (HSP), neurolathyrism, Konzo, Tay-Sachs disease, Sandhoff disease, progressive muscular atrophy (PMA), monomelic amyotrophy, spinal muscular atrophy (SMA), spinal-bulbar muscular atrophy (SBMA), progressive bulbar palsy (PBP), post-poliomyelitis syndrome, post-irradiation syndrome, stiff-person syndrome, disorders of the motor units resulting from an accident, myasthenia gravis, and Eaton-Lambert syndrome, comprising administering to a patient in need thereof an effective amount of a sulphate salt of N-(3-(4-(3-(diisobutylamino) propyl) piperazin-1-yl) propyl)-1H-benzo[d]imidazol-2-amine and pharmaceutically acceptable solvates thereof.

3. A method according to claim 1, wherein the sulphate salt has Formula I Formula I

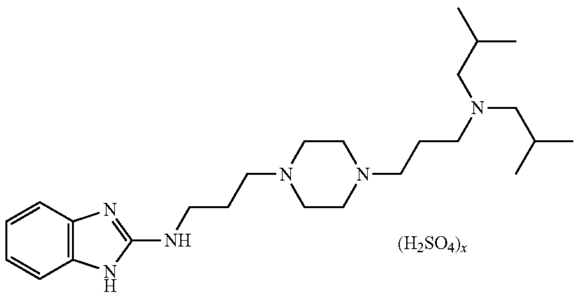

wherein x is 0.5 to 4, and pharmaceutically acceptable solvates thereof.

4. A method according to claim 3, characterized in that x is about 2.

5. A method according to claim 4, wherein the sulphate salt is N-(3-(4-(3-(diisobutylamino) propyl) piperazin-1-yl) propyl)-1H-benzo[d]imidazol-2-amine di-sulphate.

6. A method according to claim 1, wherein the motor neuron diseases and neuromuscular junction disorders are selected from non-FTD amyotrophic lateral sclerosis, primary lateral sclerosis (PLS), hereditary spastic paraplegia (HSP), progressive muscular atrophy (PMA), monomelic amyotrophy, spinal muscular atrophy (SMA), spinal-bulbar muscular atrophy (SBMA), progressive bulbar palsy (PBP), myasthenia gravis, Eaton-Lambert syndrome, and disorders of the motor units resulting from an accident.

7. A method according to claim 6, wherein the motor neuron diseases are selected from non-FTD amyotrophic lateral sclerosis, primary lateral sclerosis (PLS), hereditary spastic paraplegia (HSP), spinal muscular atrophy (SMA), spinal-bulbar muscular atrophy (SBMA), and progressive bulbar palsy (PBP).

8. A method according to claim 7, wherein the motor neuron disease is non-FTD amyotrophic lateral sclerosis.

9. A method according to claim 2, wherein the sulphate salt has Formula I Formula I

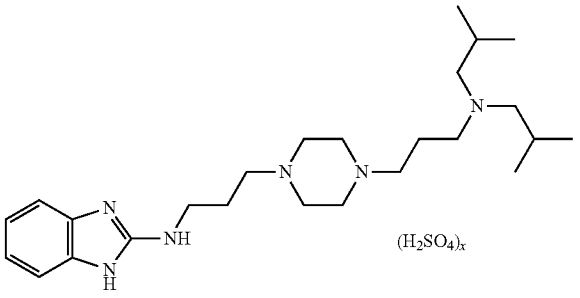

wherein x is 0.5 to 4, and pharmaceutically acceptable solvates thereof.

10. A method according to claim 9, characterized in that x is about 2.

11. A method according to claim 10, wherein the sulphate salt is N-(3-(4-(3-(diisobutylamino) propyl) piperazin-1-yl) propyl)-1H-benzo[d]imidazol-2-amine di-sulphate.

12. A method according to claim 2, wherein the motor neuron diseases and neuromuscular junction disorders are selected from non-FTD amyotrophic lateral sclerosis, primary lateral sclerosis (PLS), hereditary spastic paraplegia (HSP), progressive muscular atrophy (PMA), monomelic amyotrophy, spinal muscular atrophy (SMA), spinal-bulbar muscular atrophy (SBMA), progressive bulbar palsy (PBP), myasthenia gravis, Eaton-Lambert syndrome, and disorders of the motor units resulting from an accident.

13. A method according to claim 12, wherein the motor neuron diseases are selected from non-FTD amyotrophic lateral sclerosis, primary lateral sclerosis (PLS), hereditary spastic paraplegia (HSP), spinal muscular atrophy (SMA), spinal-bulbar muscular atrophy (SBMA), and progressive bulbar palsy (PBP).

14. A method according to claim 13, wherein the motor neuron disease is non-FTD amyotrophic lateral sclerosis.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial sequence
<220> FEATURE:
<223> OTHER INFORMATION: SOD1 primer

<400> SEQUENCE: 1

catcagccct aatccatctg a                                              21


<210> SEQ ID NO 2
<211> LENGTH: 21
```

-continued

```
<212> TYPE: DNA
<213> ORGANISM: Artificial sequence
<220> FEATURE:
<223> OTHER INFORMATION: SOD1 primer

<400> SEQUENCE: 2

cgcgactaac aatcaaagtg a                                              21
```